(12) United States Patent
He et al.

(10) Patent No.: US 7,242,745 B2
(45) Date of Patent: Jul. 10, 2007

(54) X-RAY DIFFRACTION SCREENING SYSTEM CONVERTIBLE BETWEEN REFLECTION AND TRANSMISSION MODES

(76) Inventors: Bob Baoping He, 7425 W. Valley Ridge Dr., Madison, WI (US) 53719; Ryan C. Bollig, 6243 State Rd. 73, Marshall, WI (US) 53559

( * ) Notice: Subject to any disclaimer, the term of this patent is extended or adjusted under 35 U.S.C. 154(b) by 55 days.

(21) Appl. No.: 11/184,551

(22) Filed: Jul. 19, 2005

(65) Prior Publication Data

US 2006/0023838 A1   Feb. 2, 2006

Related U.S. Application Data

(60) Provisional application No. 60/592,037, filed on Jul. 29, 2004.

(51) Int. Cl.
*G01N 23/20* (2006.01)
(52) U.S. Cl. ........................................................ 378/81
(58) Field of Classification Search ................ 378/70, 378/71, 79, 81
See application file for complete search history.

(56) References Cited

U.S. PATENT DOCUMENTS 6,111,930 A    8/2000  Schipper ...................... 378/79
6,859,520 B2 *  2/2005  He et al. ...................... 378/79
2003/0108152 A1  6/2003  Bowen et al. ................. 378/74
2004/0208284 A1* 10/2004  Brugemann et al. .......... 378/70

FOREIGN PATENT DOCUMENTS

EP      1 469 305 A1    10/2004
WO     WO 03/081221 A   10/2004

* cited by examiner

*Primary Examiner*—Courtney Thomas
(74) *Attorney, Agent, or Firm*—Law Offices of Paul E. Kudirka

(57) ABSTRACT

An X-ray diffraction apparatus provides analysis in either transmission or reflective mode and easy conversion between the two modes. An X-ray source and X-ray detector are each connected to a different circle of a goniometer. The two circles may be rotated independently to position the source and detector on the same side of a sample library for reflection mode operation, or on opposite sides of the sample library for transmission mode operation. The sample library has a horizontal orientation that allows open sample containers of the library to maintain the sample without spillage, and it connects to an XYZ stage that can move in three dimensions. The system may use a beamstop, and the goniometer and XYZ stage be motorized and controlled for automated sample analysis.

30 Claims, 2 Drawing Sheets

X-RAY DIFFRACTION SCREENING SYSTEM CONVERTIBLE BETWEEN REFLECTION AND TRANSMISSION MODES

CROSS-REFERENCE TO RELATED APPLICATION

This application takes priority from U.S. Provisional Patent Application Ser. No. 60/592,037, filed Jul. 29, 2004.

FIELD OF THE INVENTION

The present invention relates, generally, to X-ray diffraction screening and, more particularly, to X-ray diffraction screening of sample libraries for combinatorial chemistry.

BACKGROUND OF THE INVENTION

Combinatorial chemistry refers to techniques to collect, test, and store the resulting data for a material library containing tens, hundreds or even thousands of different materials or compounds. Combinatorial investigations require rapid screening techniques to test and evaluate variations of composition, structure and property within a material library. X-ray diffraction is one of the most suitable screening techniques because abundant information can be revealed from the diffraction pattern, and the technique is fast and non-destructive.

Combinatorial screening with X-ray diffraction may be performed in reflection mode. In reflection mode, both an X-ray source and an X-ray detector are located to the same side of a sample being examined. For many samples or sample libraries, only one side of the sample is exposed and, therefore, X-ray diffraction can only be done in reflection mode. In some other cases, although two opposing sides of a sample are exposed, the thickness of the sample is beyond the penetration capability of the X-ray energy from the source and, again, only reflection mode diffraction is possible.

Many combinatorial chemistry applications require X-ray diffraction screening in the low Bragg angle range, such as the search for catalysts and new drugs. In the low angle diffraction measurement, the incident X-ray beam is spread over the sample surface into an area much larger than the size of the original X-ray beam. In combinatorial screening applications, sample cells are located close each other. Therefore, the spread beam may cause cross contamination in the collected diffraction data. There are two ways to overcome these problems. One way is to use a knife-edge to limit the diffracted area. The details of such a knife-edge may be found in U.S. Pat. No. 6,718,008, the substance of which is incorporated herein by reference. Another way to avoid cross-contamination is to perform the X-ray diffraction screening in transmission mode.

In transmission mode X-ray diffraction measurement, an incident X-ray beam is directed toward one surface of the specimen, and diffracted X-rays are emitted from a surface on the opposite side of the specimen. The incident beam is typically perpendicular to the sample surface so that the irradiated area on the specimen is limited to a size comparable to the X-ray beam size, allowing the X-ray beam to remain concentrated en route to the intended measuring area. Since the X-ray beam is focused in a relatively small spot on an incident surface of the sample, the risk of cross contamination between sample locations is minimized. An X-ray diffraction system dedicated to transmission mode operation is disclosed in U.S. Pat. No. 6,859,520.

Most existing X-ray diffractometers for combinatorial screening are dedicated to operation in either reflection mode or transmission mode. The sample library in a combinatorial screening system is typically aligned in horizontal direction, and during the screening process the sample library retains its horizontal orientation. This is necessary for holding powder samples or liquid samples without spillage. Otherwise if, for example, reflection mode diffraction data was to be collected on a system configured for transmission mode analysis, the sample library would have to be rotated away from the horizontal position, and the powder or liquid samples could fall out of the sample containers and/or be cross-contaminated with other samples. The same would be true if a transmission mode system were to be used for reflection mode diffraction.

SUMMARY OF THE INVENTION

In accordance with the present invention, an X-ray diffraction apparatus is provided that allows X-ray diffraction analysis in either transmission or reflection mode, and provides for an easy and automatic conversion between the two modes. This differs from prior art systems, which are typically dedicated to either reflection mode or transmission mode. In the present invention, the system runs at optimum configuration for both reflection and transmission modes, and the sample library is always in the horizontal position.

The apparatus has a mounting assembly that maintains a sample holder, e.g., a sample library, in a horizontal orientation along a horizontal axis. An X-ray source assembly directs X-ray energy toward the sample holder, and an X-ray detector assembly detects X-ray energy diffracted from the sample. To allow relative repositioning of the source and detector, a movement assembly is provided that allows movement of at least one of these components. That is, with the movement assembly, either the source assembly or the detector assembly may be moved to relocate it to one side of the sample holder or the other. In a first position, the source and detector are on the same side of the horizontal axis of the sample library to allow operation in reflection mode. When the movement assembly is moved to a second position, the source and detector are on opposite sides of the horizontal axis, thereby allowing operation in transmission mode. Depending on the particular arrangement of the system, either the source or the detector may be moved with the movement assembly to convert the system from reflection mode to transmission mode.

In a particular embodiment, the system is constructed using a goniometer having at least two circles that are independently rotatable. The X-ray source may be connected to a first circle of the goniometer that is movable along a predetermined path. Movement of the source assembly relocates it from a first source position, in which the X-ray energy is directed toward an upper surface of the sample holder, and a second source position, in which the X-ray energy is directed toward a lower surface of the sample holder. This allows the change from reflection to transmission mode. The X-ray detector may be connected to a second circle of the goniometer to allow it to be moved as well. In such a case, the movement of the detector might allow changes in the detector swing angle. Alternatively, the source could remain on the same side of the sample holder axis, while the detector is rotated from one side to the other to change from reflection mode to transmission mode.

In one embodiment, the X-ray source assembly includes accompanying optics, and may be connected to an inner circle of the goniometer along with a video assembly. The detector may be connected to an outer circle of the goniometer, such that it moves free of the source and video components. A sample holder, or library, has a horizontal orientation that allows open sample containers of the library to maintain the sample without spillage. The sample library resides on a sample support that is part of the mounting assembly. The mounting assembly may also include an XYZ stage that can be adjusted to move the sample support in three dimensions, while maintaining its horizontal orientation. The XYZ stage may be offset from the location of the sample support so as to keep it from interfering with the other system components.

In one variation of the invention, counterweights are provided for the components connected to the inner and outer circles of the goniometer. These counterweights can be located on the back side of the goniometer, that is, to the sides of the first and second circles opposite the sides to which the source assembly and detector assembly components are connected. A counterweight for the inner circle may have a rotational connection to the inner circle that follows a rotational axis of the goniometer. A counterweight for the outer circle may be attached to a rotational connection located on the back side of the goniometer, and the rotational connection may be connected to the outer circle via a connecting rod that passes around the outside of the goniometer.

In operation, the X-ray diffraction system may be used in either reflection mode or transmission mode. For example, in reflection mode, the X-ray source assembly and video assembly are located above the sample library, that is, above a horizontal axis along which the sample library resides. In this case, the detector is located on the same side of the horizontal axis, and X-ray energy directed toward the upper surface of a sample being examined is diffracted toward the detector. In transmission mode, the X-ray source and video assembly are located below the sample, on the opposite side of the horizontal axis from the detector. The X-ray energy of the source is transmitted through the sample and, upon reaching the opposite side, some of it is diffracted toward the detector. The system may be changed from reflection mode to transmission mode by rotating one circle of the goniometer. Prior to this rotation, it may be desirable to use the XYZ stage to adjust the position of the sample support so that it does not interfere with the movement of the X-ray source and video assembly. For example, the XYZ stage may be adjusted so that the sample support is moved away from an arcuate path followed by the source assembly or detector assembly as the circle to which it is secured is rotated. A beamstop may also be included for use in the transmission mode, and the beamstop may be removable or movable from an operating position to a safe position which keeps it from contacting other system components during conversion to the reflection mode.

The movement of all of the components of the diffractometer may be computer controlled to allow automation of the detection of the entire sample library. A controller can be linked to motors that cause the rotation of the goniometer circles, as well as to motors that cause the translational movements of the XYZ stage. The controller could also operate the X-ray source and detector, for controlling the analysis of an individual sample, and use the video system for positioning the sample. With these different functionalities available, the controller could move the sample support so as to progressively align each of the samples of the sample library in the appropriate position for examination. If it was desired to change between transmission mode and reflection mode for any or all of the samples, the controller could execute the necessary movement of the system components to accomplish this. In this way, the system could be completely automated.

BRIEF DESCRIPTION OF THE DRAWINGS

The above and further advantages of the invention may be better understood by referring to the following description in conjunction with the accompanying drawings in which.

DETAILED DESCRIPTION

Figure 1:
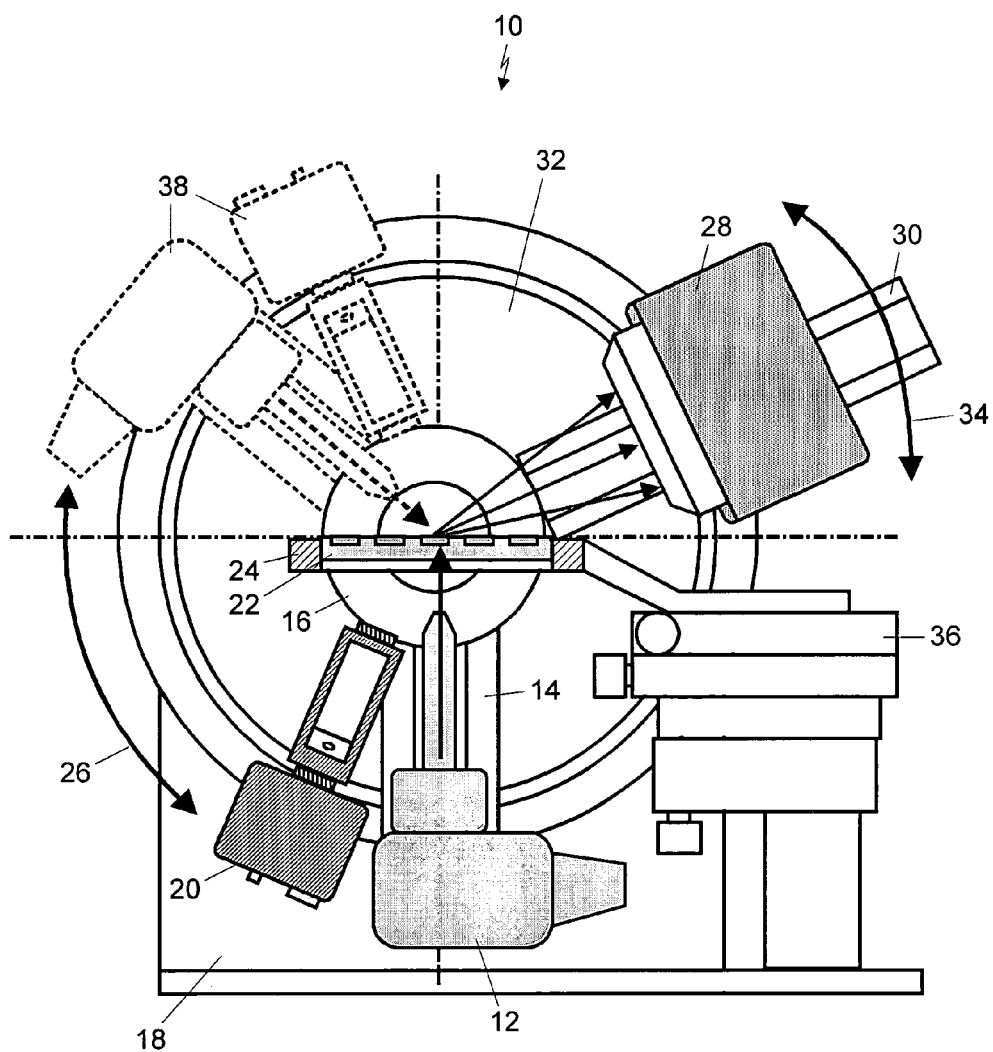
FIG. 1 is a schematic front view of an X-ray diffractometer according to the present invention.

FIG. 1 shows an illustration of the front view of an embodiment of the X-ray diffractometer 10 according to the present invention. In this arrangement, the X-ray source and optics 12 are mounted on a dovetail track 14. The dovetail track is fixed on the inner circle 16 of a vertical goniometer 18. A laser video assembly 20 is also attached to the inner circle of the goniometer. The laser video system 20 is of known configuration, and may be like that described in U.S. Pat. No. 5,359,640, which is incorporated herein by reference. A sample library 22 is supported by a sample support 24. The sample library contains a plurality of individual sample locations, which may be a series of adjacent sample wells. In operation, each of the samples is investigated individually, as the sample library may be moved to reposition the samples for each investigation.

The X-ray source, optics, and video assembly, being connected to the inner circle 16 of the goniometer 18, may be moved between a transmission mode position and a reflection mode position by rotation of the inner circle 16 as indicated by arrow 26. A two-dimensional X-ray detector 28 is mounted on a dovetail track 30 along which the detector may slide to change the distance between the sample being examined and the detector. The dovetail track 30 is attached to the outer circle 32 of the goniometer 18. The detector swing angle may thereby be changed by rotation of the outer circle as indicated by arrow 34.

The sample support 24 is attached to an offset XYZ stage 36. The XYZ stage allows the sample support 24 to be moved in three dimensions, but locates the movement mechanism away from the center of the instrument, so as to yield space for the X-ray source and optics for transmission mode operation. In a typical experiment, the XYZ stage 36 is adjusted to position a first sample in position to be examined. After the X-ray diffraction analysis of that sample is completed, the XYZ stage is adjusted to position the next sample at the proper location. This process continues from sample to sample until all of the samples in the library are examined. Since the sample support 24 is not rotated from its horizontal orientation, the primary movement of the XYZ stage is in the "x" and "y" directions, repositioning the sample support so that the examination of each sample can be conducted one by one. Movement of the XYZ stage 36 in the "z" direction is limited, and allows minor repositioning of the sample support 24 in a vertical direction relative to the X-ray source and optics 12 and the X-ray detector 28.

The conversion between reflection mode and transmission mode can be done manually, but it can also be done automatically under computer control. A controller would have control over the rotation of the inner circle 16 of the goniometer, as well as the movement of the XYZ stage. Thus, when it is desired to change between reflection mode and transmission mode, the controller moves the XYZ stage 36 and the sample support 24 into a safe position to avoid collision with the components of the X-ray optics during the mode conversion. The controller can also be used to control the data collection process, initiating the transmission of the X-ray beam from the X-ray source, the detection of the diffracted X-ray energy by the detector, and the storage and/or analysis of the detected signal. In this way, the entire analysis process may be automated.

In FIG. 1, the dashed line components at 38 indicate the X-ray source and optics 12 and video assembly 20 when positioned for reflection mode operation. As shown, in this position, X-ray energy is directed to the top of the sample under investigation, and diffracted X-ray energy is detected by the detector 28. When it is desired to change to transmission mode operation, the controller initiates movement of the XYZ stage 36 so as to move sample support 24 toward the XYZ stage and, therefore, out of the rotation path of the X-ray source and optics 12 and video assembly 20. The controller then initiates a rotation of the inner circle 16 of the goniometer so as to move the X-ray source and optics 12 and video assembly 20 along the path of the arrow 26 until they reach the transmission mode position shown in the figure. In this position, X-ray energy from the X-ray source is directed through the bottom of the sample under investigation, and X-ray energy diffracted from the upper surface of the sample is detected by detector 28. Definitions of the geometry and safety limits for all the moving parts of the system may be stored in software that runs in conjunction with the controller operation, and all would be updated automatically when the conversion from one mode to the other occurs.

In an alternative embodiment, it may be the detector that is moved from one side of the sample library to the other. In the arrangement shown in FIG. 1, the X-ray source and optics and video assembly could remain at the position 38 shown in dashed lines in the figure. The XYZ stage could then be moved out of the way, or could be located, more conveniently, on the opposite side of the goniometer (i.e., on the left side relative to the orientation of the figure). The outer circle 32 of the goniometer may then be rotated to move the detector 28 to a position below the sample library. With the source and optics remaining above the sample library, analysis in transmission mode may then commence.

During data collection or conversion between reflection and transmission mode, the X-ray source and optics assembly, the video assembly and detector assembly may rotate about the horizontal axis of the vertical goniometer. The weights of both assemblies may produce a variable load on the bearings and driving gears of the goniometer depending on the rotation angles. This could both put undue wear on the goniometer components, and could possibly limit the rotational precision of the goniometer. In the present invention, therefore, it may be desirable to use counterweight balances connected to the inner and outer circles.

Figure 2:
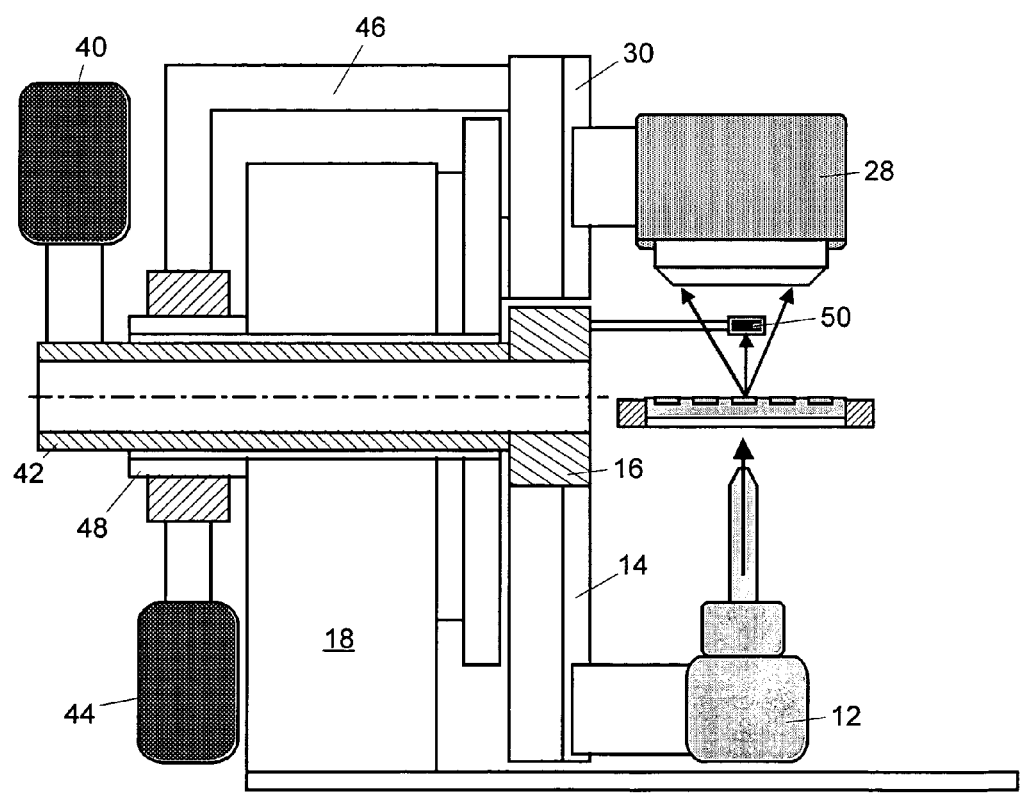
FIG. 2 is a schematic, cross-sectional side view of the X-ray diffractometer of FIG. 1.

FIG. 2 is a cross-sectional side view of a system according to the present invention, with the section being taken along the rotational center of the two-circle vertical goniometer. Those skilled in the art will recognize that, as with FIG. 1, certain system components may be omitted from the figure to provide clarity. As shown, the X-ray source and optics 12 are coupled to a counterweight 40 through the dovetail track 14, the inner circle 16, and a coupling axis 42 through the center of the vertical goniometer 18. The detector 28 is coupled to a counterweight 44 through the dovetail track 30 and a connecting rod 46. The connecting rod 46 is coupled to the counterweight 44 via a rotational bearing 48, which allows rotation about the goniometer axis. Thus, as the outer circle of the goniometer is rotated to reposition the detector 28, the counterweight 44 is correspondingly rotated on the opposite side of the goniometer. Likewise, as the inner circle 16 is rotated to reposition the X-ray source and the video assembly, there is a corresponding rotation of the counterweight 40. These counterweights minimize the forces on the goniometer rotational components, which could otherwise reduce rotational precision and produce undue wear.

Also shown in FIG. 2 is a beamstop 50. The beamstop is positioned between the sample under investigation and the detector when the detector 28 is positioned relatively close to the transmission axis of the X-ray source. Such a position might occur, for example, when small-angle scattering experiments were being conducted. Location of the beamstop 50 in this position prevents any portion of the X-ray beam from the X-ray source that passes through the sample from directly hitting the detector, which could otherwise saturate the detector and make measurements of the diffracted X-ray energy more difficult. The beamstop 50 may be mounted on the inner circle 16 above the sample library 22 and sample support 24. The beamstop is not necessary when the system is operated in the reflection mode, and may therefore be removed from the position shown in FIG. 2. The beamstop may be attached and removed manually or, alternatively, may be motorized to be moved between a working position and a "safe" position. In the working position, as shown in the figure, the beamstop blocks the incident X-ray energy as described above. In the safe position, the beamstop is drawn back, or possibly folded up, toward the goniometer so that it will not make contact with the XYZ stage when the inner circle is rotated to position the system for the reflection mode.

While the invention has been shown and described with reference to a preferred embodiment thereof, it will be recognized by those skilled in the art that various changes in form and detail may be made herein without departing from the spirit and scope of the invention as defined by the appended claims.

What is claimed is:

1. An X-ray diffraction apparatus for analyzing a sample on a sample holder, the apparatus comprising:
   a mounting assembly that maintains the sample holder along a horizontal axis, such that one side of the sample holder is located to a first side of the axis and an opposite side of the sample holder is located to a second side of the axis;
   an X-ray source that directs X-ray energy toward the sample holder;
   an X-ray detector that detects X-ray energy diffracted from the sample; and
   a movement assembly that allows movement of one of the source and detector along a predetermined path between a first position, in which the source and detector are on same side of the horizontal axis, and a second position, in which the source and detector are on opposite sides of the horizontal axis from each other and that prevents any collisions between the source, the detector and any other mechanical parts connected thereto from occurring during the movement.

2. An apparatus according to claim 1 wherein the movement assembly allows movement of the X-ray source along said predetermined path.

3. An apparatus according to claim 1 wherein the movement assembly allows movement of the X-ray detector along said predetermined path.

4. An apparatus according to claim 1 further comprising a goniometer to which the X-ray source assembly and the X-ray detector assembly are connected.

5. An apparatus according to claim 4 wherein the source assembly is connected to a first circle of the goniometer and the detector assembly is connected to a second circle of the goniometer, and wherein each of the first and second circles is rotatable independently.

6. An apparatus according to claim 5 further comprising a video assembly that is focused on the sample and that is connected to the first circle of the goniometer.

7. An apparatus according to claim 5 further comprising a counterweight attached to the first circle of the goniometer that counterbalances the source assembly.

8. An apparatus according to claim 7 wherein the counterweight is located to a side of the first circle opposite that to which the source assembly is connected.

9. An apparatus according to claim 8 wherein the counterweight is connected to the first circle via a rotary connection aligned with a central axis of the goniometer.

10. An apparatus according to claim 5 further comprising a counterweight attached to the second circle of the goniometer that counterbalances the detector assembly.

11. An apparatus according to claim 10 wherein the counterweight is located to a side of the second circle opposite that to which the detector assembly is connected.

12. An apparatus according to claim 11 wherein the counterweight is connected to the second circle via a connecting rod that extends around an outer surface of the goniometer.

13. An apparatus according to claim 1 wherein the mounting assembly is movable to allow relocation of the sample holder between a sample position and an alternate position.

14. An apparatus according to claim 13 wherein the mounting assembly is movable in at least two perpendicular directions.

15. An apparatus according to claim 13 wherein, when the sample holder is in the sample position, complete movement of at least one of the source assembly and the detector assembly is obstructed, and wherein such obstruction is removed when the sample holder is in the alternate position.

16. An apparatus according to claim 1 wherein the sample is a first sample, and wherein the sample holder comprises a plurality of sample locations for retaining a plurality of samples simultaneously.

17. An apparatus according to claim 16 wherein, at any given time, one of the plurality of samples is positioned at a sample site to which X-ray energy from the source is directed and from which diffracted X-ray energy is detected by the detector, and wherein the mounting assembly is movable to reposition the sample holder to change which of the plurality of samples is at the sample site.

18. An apparatus according to claim 1 further comprising motors that are used for moving the X-ray source assembly and the detector assembly and a controller that automatically controls the motors.

19. An apparatus according to claim 1 further comprising a beamstop located between the sample and the detector that blocks non-diffracted X-ray energy from reaching the detector.

20. An apparatus according to claim 1 further comprising a video assembly positioned to allow viewing of the sample.

21. An X-ray diffraction apparatus for analyzing a sample positioned at a sample site, the sample being located on a sample holder having a plurality of sample locations, the apparatus comprising:
    a goniometer;
    a mounting assembly that maintains the sample holder in a horizontal orientation and that is movable in at least two directions to reposition the sample holder to change which of the plurality of sample locations is at the sample site;
    an X-ray source assembly that is connected to a first circle of the goniometer and that has an X-ray source that directs X-ray energy toward the sample holder, the source assembly being movable with movement of the first goniometer circle along a predetermined path to relocate the X-ray source from a first source position in which the X-ray energy is directed toward an upper surface of the sample holder to a second source position in which the X-ray energy is directed toward a lower surface of the sample holder;
    an X-ray detector assembly that is connected to a second goniometer circle of the goniometer and that has an X-ray detector that detects X-ray energy diffracted from an upper surface of the sample, the detector assembly being movable with the second goniometer circle; and
    means for preventing any collisions between the X-ray source assembly, the X-ray detector assembly and any other mechanical parts connected thereto from occurring during movement of the X-ray source and the X-ray detector.

22. An X-ray diffraction apparatus for analyzing a sample on a sample holder, the apparatus comprising:
    a mounting assembly that locates the sample holder at a predetermined location;
    an X-ray source that directs X-ray energy toward the sample holder;
    an X-ray detector that detects X-ray energy diffracted from the sample; and
    a goniometer to which the X-ray source and the X-ray detector are secured, the goniometer having at least two circles that are rotatable independently of each other and that each have a mounting side to which either the X-ray source or the X-ray detector may be secured, each of the circles also being connected to a respective counterweight that is located on a side of that circle opposite its mounting side, the counterweight for a first of the circles being connected to the first circle via a rotary connection aligned with a central axis of the goniometer, and the counterweight for a second of the circles being connected to the second circle via a connecting rod that extends around an outer surface of the goniometer in order to prevent any collisions between the X-ray source assembly, the X-ray detector assembly, the counterweights and the connecting rod from occurring during rotation of the X-ray source and the X-ray detector.

23. An X-ray diffraction apparatus according to claim 22 wherein the X-ray source is secured to the first circle of the goniometer and the X-ray detector is secured to the second circle.

24. An X-ray diffraction apparatus according to claim 23 further comprising a video system secured to the first circle of the goniometer that captures an image of the sample.

25. An X-ray diffraction apparatus according to claim 22 wherein the first and second circles of the goniometer have a first relative position in which the X-ray source and the X-ray detector are located to the same side of the sample, thereby allowing reflection-mode operation of the system, and a second relative position in which the X-ray source and the X-ray detector are located on opposite sides of the sample, thereby allowing transmission-mode operation of the system.

26. A method of analyzing a sample on a sample holder, the method comprising:
    locating the sample holder on a mounting assembly that maintains the sample holder along a horizontal axis, with one side of the sample holder being located to a first side of the axis and an opposite side of the sample holder being located to a second side of the axis;

directing X-ray energy toward the sample holder with an X-ray source;

detecting X-ray energy diffracted from the sample with an X-ray detector; and moving one of the source and detector along a predetermined path between a first position, in which the source and detector are on the same side of the horizontal axis, and a second position, in which the source and detector are on opposite sides of the horizontal axis from each other and preventing any collisions between the source, the detector and any other mechanical parts connected thereto from occurring during the movement.

27. A method according to claim 26 further comprising securing the source assembly to a first circle of a goniometer and securing the detector assembly to a second circle of the goniometer, each of the first and second circles being rotatable independently.

28. A method according to claim 27 further comprising attaching a source counterweight to the first circle of the goniometer to counterbalance the source assembly, the source counterweight being located to a side of the first circle opposite that to which the source assembly is secured.

29. A method according to claim 28 further comprising attaching a detector counterweight to the second circle of the goniometer to counterbalance the detector assembly, wherein the detector counterweight is located to a side of the second circle opposite that to which the detector assembly is secured, and wherein the source counterweight is connected to the first circle via a rotary connection that passes through the goniometer.

30. A method according to claim 26 wherein the mounting assembly is movable in at least two perpendicular directions.

* * * * *